(12) United States Patent
Sachdeva et al.

(10) Patent No.: US 9,232,988 B2
(45) Date of Patent: *Jan. 12, 2016

(54) ORTHODONTIC DEVICE

(76) Inventors: Rohit C L Sachdeva, Plano, TX (US); Kunio Chikami, Kochi (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/506,633

(22) Filed: May 5, 2012

(65) Prior Publication Data

US 2014/0045136 A1 Feb. 13, 2014

Related U.S. Application Data

(63) Continuation-in-part of application No. 11/996,090, filed as application No. PCT/JP2006/314064 on Jul. 14, 2006, now Pat. No. 8,272,867.

(30) Foreign Application Priority Data

Jul. 20, 2005 (JP) ................................. 2005-209524

(51) Int. Cl.
*A61C 3/00* (2006.01)
*A61C 7/28* (2006.01)

(52) U.S. Cl.
CPC ...................................... *A61C 7/285* (2013.01)

(58) Field of Classification Search
USPC ......................................................... 433/8–16
See application file for complete search history.

(56) References Cited

U.S. PATENT DOCUMENTS

| | | | | |
|---|---|---|---|---|
| 4,498,867 A | * | 2/1985 | Kesling | 433/16 |
| 5,271,733 A | * | 12/1993 | Chikami et al. | 433/20 |
| 5,356,288 A | * | 10/1994 | Cohen | 433/8 |
| 2002/0081552 A1 | * | 6/2002 | Stanwich et al. | 433/149 |
| 2005/0255422 A1 | * | 11/2005 | Cordato | 433/10 |

* cited by examiner

*Primary Examiner* — Heidi M Eide

(57) ABSTRACT

An orthodontic bracket having a slot formed by arm parts facing each other in the vertical direction, and an inner part, inserted into the slot, having a socket for holding a wire is disclosed. The shape of the socket is designed for applying desired forces to a tooth through the wire when the bracket is attached to the tooth. Forces can be changed simply by changing the inner part; replacing the bracket attached to the tooth. When the inner part is inserted into the slot, the inner part closes the slot and it is held in the position by the arm parts; enabling the wire to be securely held in its position.

23 Claims, 19 Drawing Sheets

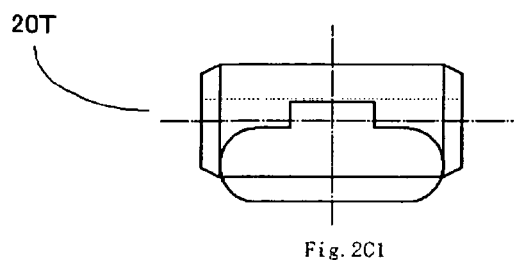
Fig. 2C1
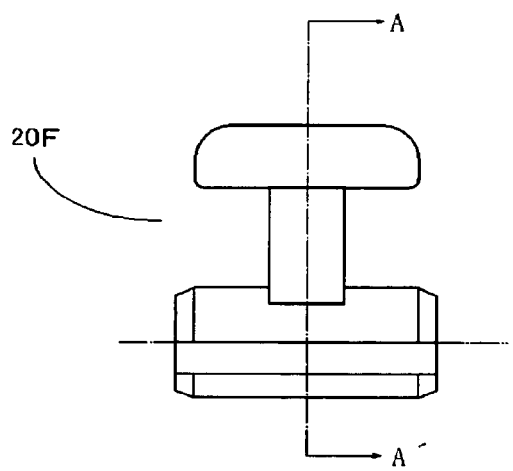
Fig. 2C2
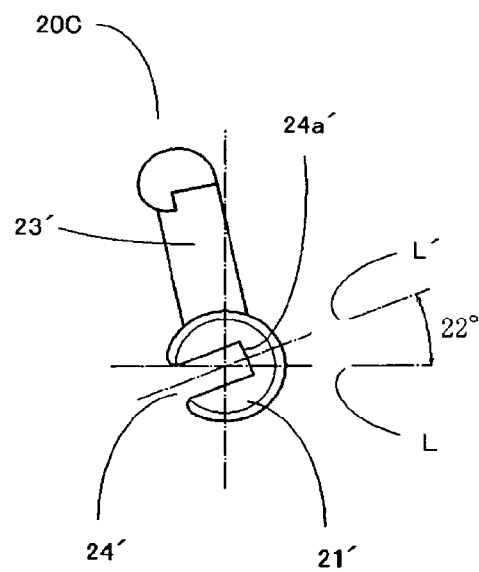
Fig. 2C3

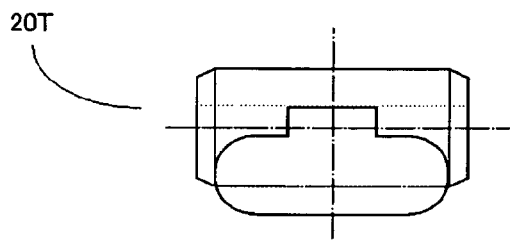
Fig. 2D1
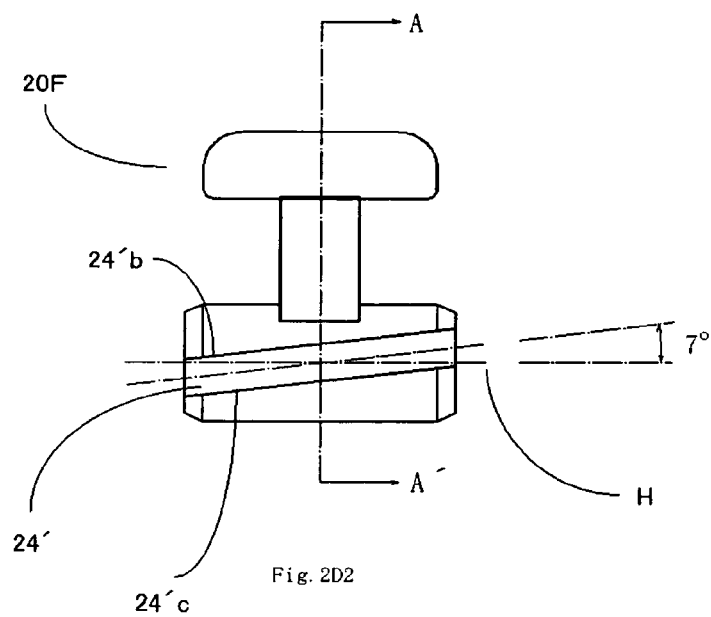
Fig. 2D2
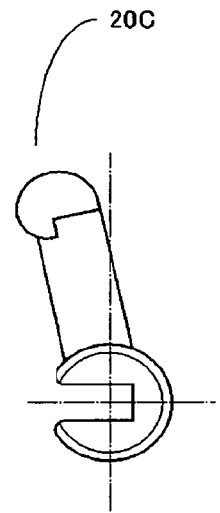
Fig. 2D3

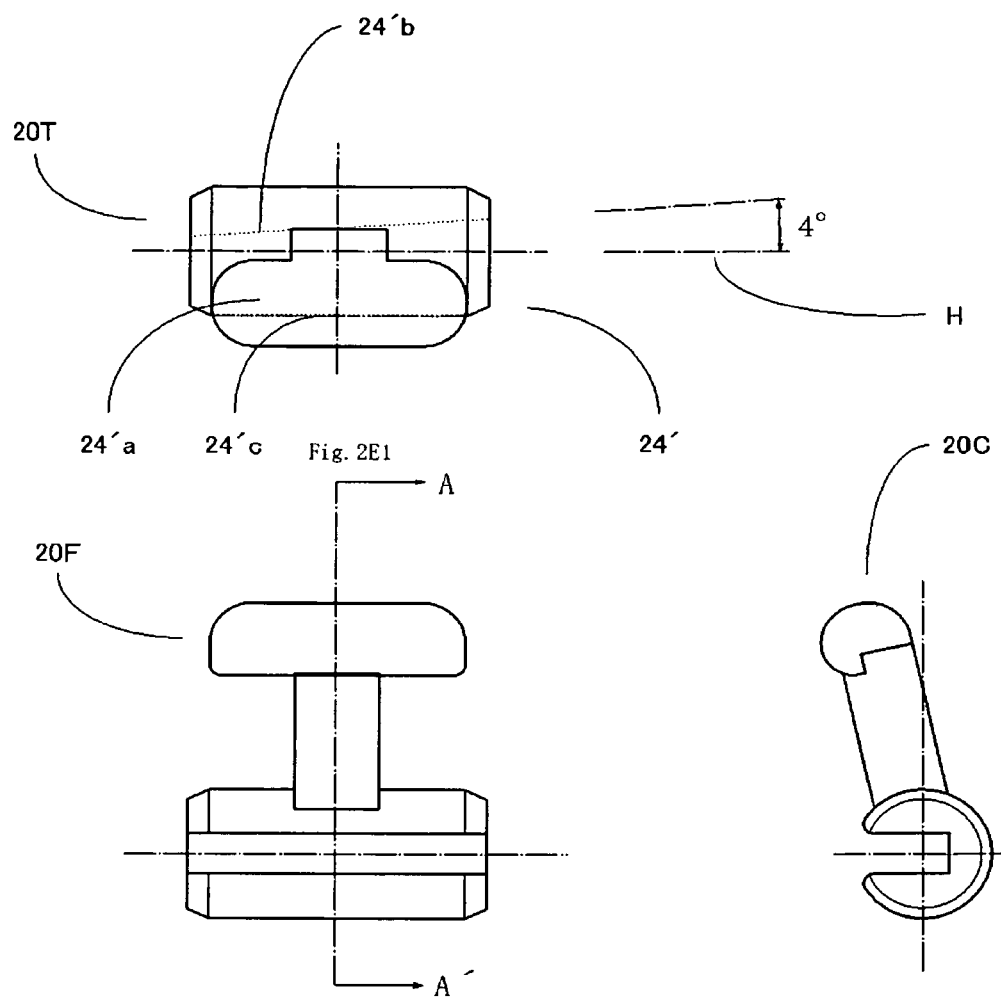
Fig. 2E1
Fig. 2E2
Fig. 2E3

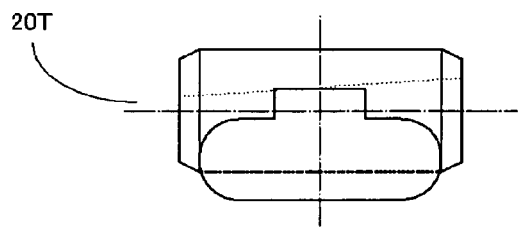
Fig. 2F1
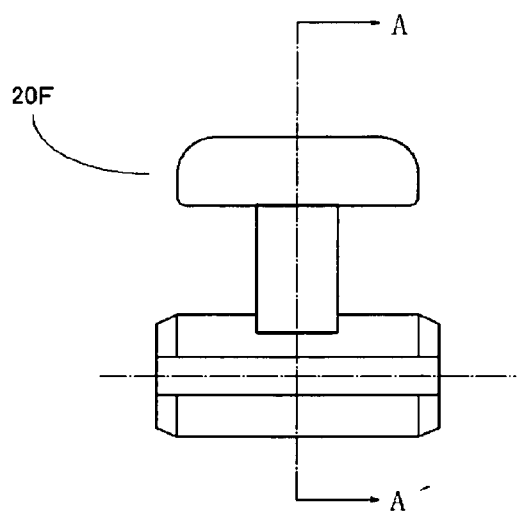
Fig. 2F2
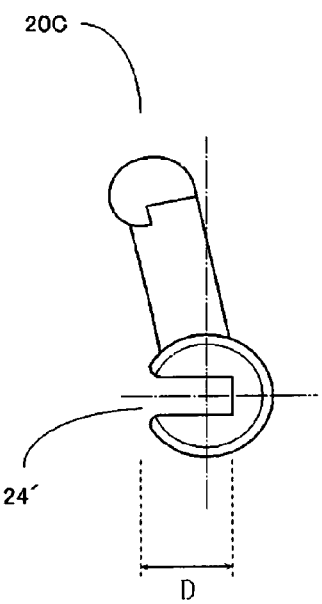
Fig. 2F3

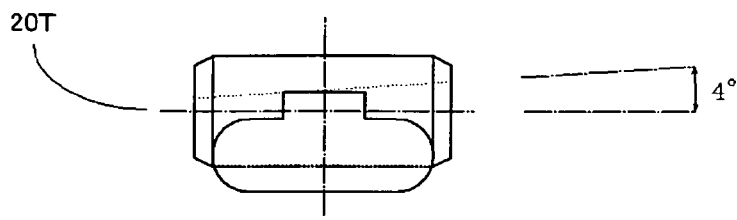
Fig. 2G1
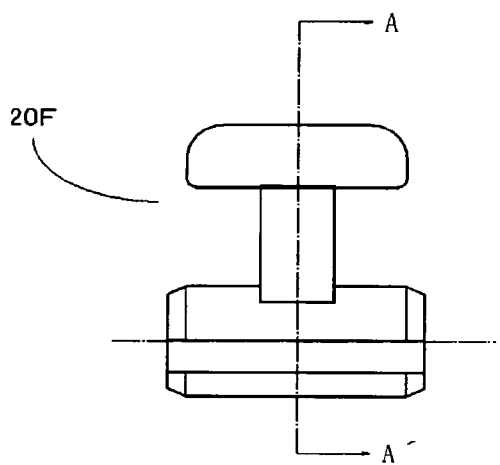
Fig. 2G2
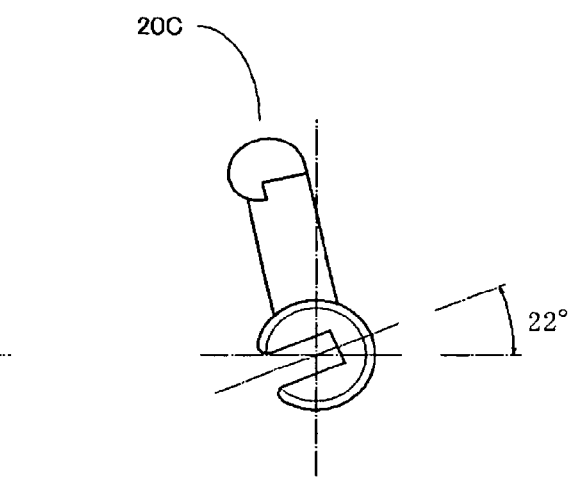
Fig. 2G3

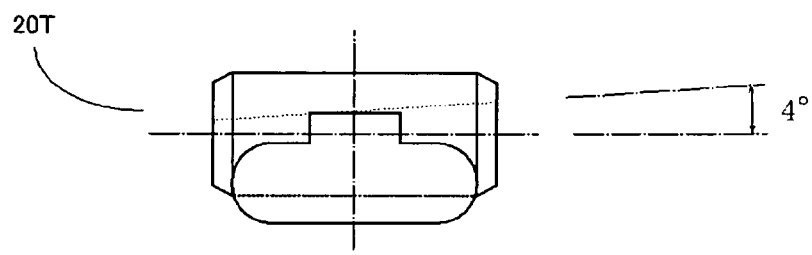
Fig. 2H1
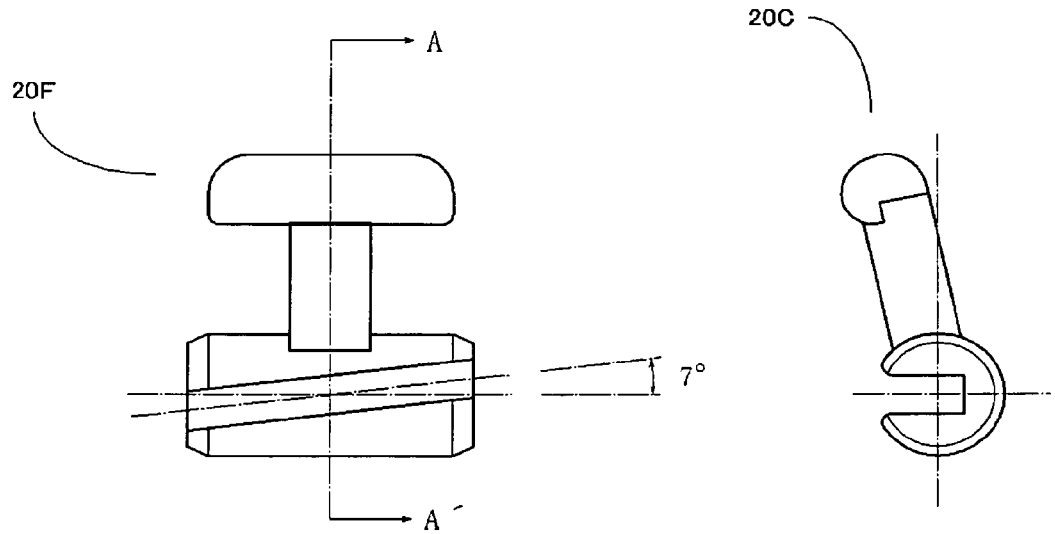
Fig. 2H2
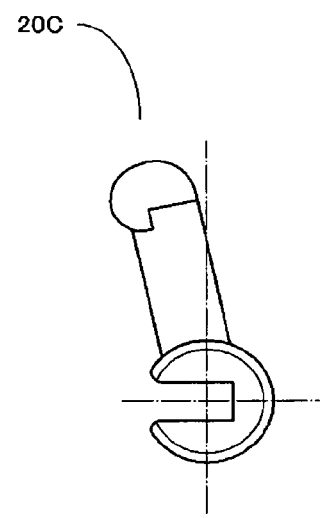
Fig. 2H3

ORTHODONTIC DEVICE

CROSS-REFERENCE TO RELATED APPLICATIONS

This application is a continuation-in-part application of prior application Ser. No. 11/996,090, filed Jan. 18, 2008 now U.S. Pat. No. 8,272,867, which is a National Stage Entry of PCT/JP2006/314064, filed Jul. 14, 2006, whose Parent Application Number is 2005-209524, Country JP, filed Jul. 20, 2005; the entire contents of each of which are incorporated by reference herein.

BACKGROUND OF THE INVENTION

A. Field of the Invention

The present invention relates to an orthodontic device.

B. Description of Related Art

A conventional orthodontic device 70 includes a bracket having a horizontal groove 72 into which a wire 80 is inserted and a vertical groove 73 formed in the front part thereof and a thin-plate-like slide member 71 inserted in the vertical groove 73 (see FIGS. 11 and 12 and the Patent Document 1). The slide member 71 can move vertically along the vertical groove 73, and the slide member 71 is moved downwardly to close the horizontal groove 72, thereby holding the wire 80 therein.

Patent Document 1: Japanese Patent Publication No. 3512466 B.

However, the slide member 71 is a thin plate and therefore is inferior in strength. In addition, most of the front surface of the slide member 71 is exposed, and therefore, the slide member 71 is likely to be subjected to an external force and can be damaged when subjected to the external force.

In addition, the slide member 71 has a shallow recess 74 formed in the back surface thereof, the bracket has a short protrusion 75 formed on the front surface thereof, and the recess 74 and the protrusion 75 are lightly engaged with each other. Therefore, there is a possibility that the slide member 71 is disengaged from and comes off the bracket when the slide member 71 is subjected to an external force. If the slide member 71 comes off the bracket, the wire 80 cannot be held in the bracket.

To minimize the possibility of the slide member 71 coming off, a spring member can be used to keep the slide member 71 engaged with the bracket by the action of the resilient force. However, the spring member incorporated in the bracket extends along the depth, so that the structure is undesirably complicated (see FIG. 18 of the Patent Document 1).

SUMMARY OF THE INVENTION

An object of the present invention is to provide an orthodontic device which does not require replacing of brackets during orthodontic treatment of a patient; and is capable of holding a wire with a simple, not complicated, structure.

In order to attain the object, according to the present invention, there is provided an orthodontic device, including: a bracket having a slot defined by an upper arm portion and a lower arm portion facing each other; and an inner part having a socket for holding a wire, in which the inner part is inserted into the slot to be held between the upper arm portion and the lower arm portion, thereby closing an opening of the slot.

With such a configuration, the wire can be held with reliability with a simple structure in which the inner part having the socket is inserted into the slot formed in the bracket. Since the structure is simple, the orthodontic device is easy to handle in treatment and can be reduced in size. Furthermore, since the inner part is held between the upper and lower arm portions facing each other, the inner part is inserted stably, so that the opening of the slot is stably kept closed, and the wire can be held with reliability. Furthermore, since the inner part has a shape suitable for insertion into the slot defined by the upper and lower arm portions facing each other, the inner part has a sufficient strength.

In the orthodontic device according to the present invention, the socket of the inner is shaped to provide desired forces to the teeth in conjunction with an archwire. The socket of the inner part may be angled. More specifically, the orthodontic device may be characterized in that the direction of opening of the socket of the inner part is angled.

With such a configuration, different torque depending on the angle of the direction of opening of the socket can be applied to a tooth. When applying a torque, if a plurality of inner parts having differently angled sockets are prepared, a desired torque can be applied only by changing the inner part without changing the bracket, which is quite preferable. In addition, the treatment can be performed easily, and the treatment time can be reduced.

Angling the direction of opening of the socket means angling the perpendicular passing through the center of the socket with respect to the perpendicular passing through the center of the base part of the inner part.

Besides torque, the socket of the inner part may be shaped to provide other types of forces as well such as angulation, rotation, and translation; either individually or in some form of combination.

Furthermore, in the orthodontic device according to the present invention, the inner part may have a handle part.

The slot and the inner part are difficult to handle in treatment because of their small sizes. However, if the inner part is provided with the handle part, the inner part can be handled by holding the handle part. As a result, the inner part can be easily handled, and the treatment can be easily performed.

Thus, an orthodontic device capable of holding a wire with a simple, not complicated, structure is provided.

BRIEF DESCRIPTION OF THE DRAWINGS

FIGS. 2C1-2H3 show different shapes of the socket of the inner part for providing different forces during orthodontic treatments of patients. Each group of these, figures, 2C1-2C3, 2D1-2D3, 2E1-2E3, 2F1-2F3, 2G1-2G3, and 2H1-2H3, shows three views of the inner part, namely, front view, top view and cross-sectional view of the inner part.

FIGS. 2C1-2C3 show the socket shaped to provide torque.

FIGS. 2D1-2D3 show the socket shaped to provide angulation.

FIGS. 2E1-2E3 show the socket shaped to provide rotation.

FIGS. 2F1-2F3 show the socket shaped to provide translation.

FIGS. 2G1-2G3 show the socket shaped to provide torque and rotation.

FIGS. 2H1-2H3 show the socket shaped to provide angulation and rotation.

FIG. 3 is a perspective view of the inner part inserted in the bracket in the embodiment 1 of the present invention;

DETAILED DESCRIPTION OF PREFERRED EMBODIMENTS

In the following, best modes for carrying out the present invention will be described with reference to the drawings showing embodiments of the present invention. FIGS. 1 to 10 show orthodontic devices according to embodiments of the present invention.

Embodiment 1

FIGS. 1 to 4 show an embodiment 1.

An orthodontic device according to the embodiment 1 includes a bracket 10 and an inner part 20 inserted in the bracket 10.

Figure 1:
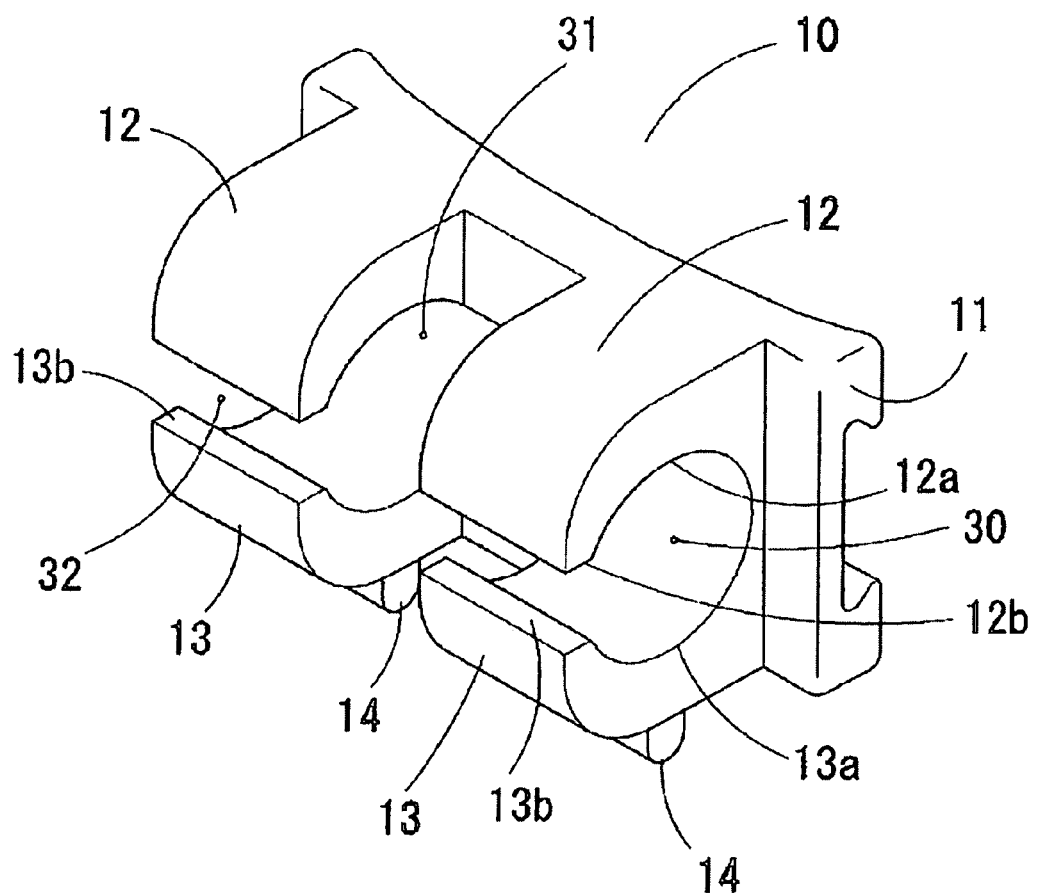
FIG. 1 is a perspective view of a bracket according to embodiments 1 and 2 of the present invention.

Referring to FIG. 1, the bracket 10 has a base portion 11 that is to be attached to the tooth surface, an upper arm portion 12 extending forward from a front surface of the base portion 11, and a lower arm portion 13 extending forward from the front surface of the base portion 11.

The base portion 11 is intended to be attached to the tooth surface with an adhesive or the like and has a protrusion, which aids in attachment of the bracket 10 to the tooth surface, on the back surface thereof.

The upper arm portion 12 and the lower arm portion 13 form a slot 30, in which the inner part 20 is inserted. Specifically, an arc-shaped surface 12a of the upper arm portion 12 and an arc-shaped surface 13a of the lower arm portion facing each other form the slot 30, which is a space having a substantially cylindrical shape.

Figure 3:
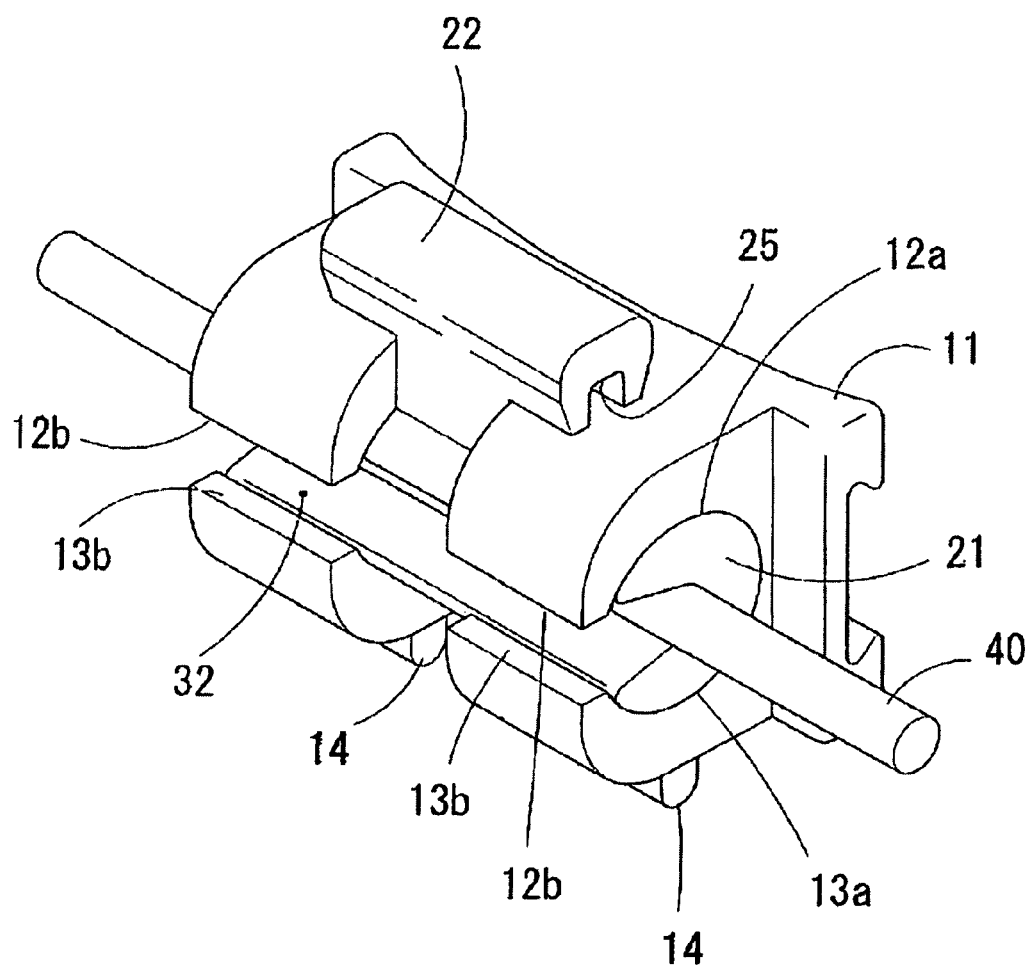

The upper arm portion 12 has the shape of a hook, and the tip part of the upper arm portion 12 is curved to cover the outer perimeter of the inner part 20, as shown in FIG. 3. Similarly, the lower arm portion 13 has the shape of a hook, and the tip part of the lower arm portion 13 is curved to cover the outer perimeter of the inner part 20. Specifically, most of the lower surface of the upper arm portion 12 is constituted by the semicircular arc-shaped surface 12a, most of the upper surface of the lower arm portion 13 is constituted by the semicircular arc-shaped surface 13a, and the two surfaces facing each other define the substantially cylindrical slot 30. When the inner part 20 is inserted in the slot 30, the inner part 20 is held between the arc-shaped surface 12a of the upper arm portion 12 and the arc-shaped surface 13a of the lower arm portion 13. The horizontal width of the slot 30 and the horizontal width of the inner part 20 are substantially equal to each other.

The slot 30 thus configured stably holds the inner part 20, and therefore, the possibility of the inner part 20 coming off the bracket 10 is reduced compared with the example of the related art described earlier. In addition, the front surface of the inner part 20 is less exposed compared with the example of the related art described earlier, and therefore, the inner part 20 is less affected by external forces and less susceptible to damage.

The upper arm portion 12 has a flat surface 12b at the tip end thereof. The lower arm portion 13 also has a flat surface 13b at the tip end thereof. The flat surface 12b of the upper arm portion 12 and the flat surface 13b of the lower arm portion 13 face each other and define an opening 32 of the slot 30. The opening 32 is a space that allows horizontal movement of a joint part 23 of the inner part 20. In addition, the opening 32 helps to insert a wire 40 into the slot 30. The vertical width of the opening 32 is substantially equal to the thickness (d) of the joint part 23.

The upper arm portion 12 and the lower arm portion 13 have a vertical slit 31 formed at the horizontal center thereof. Specifically, the upper arm portion 12 and the lower arm portion 13 have the vertical slit 31, which is a vertical notch formed to divide each of the arm portions in two. The vertical slit 31 is a space that allows vertical movement of the joint part 23 of the inner part 20. The horizontal width of the vertical slit 31 is substantially equal to the horizontal width (W) of the joint part 23.

Figure 2:
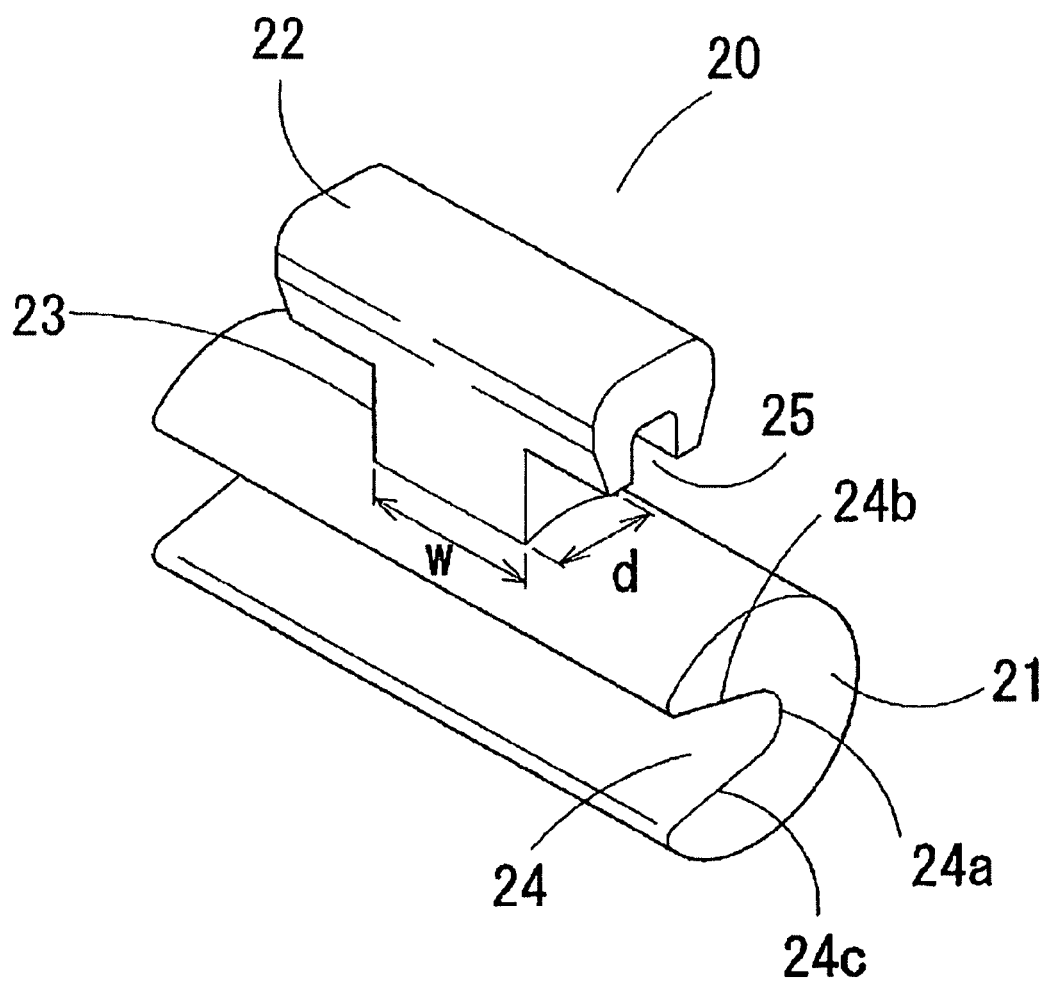
FIG. 2 is a perspective view of an inner part according to the embodiment 1 of the present invention.

Referring to FIG. 2, the inner part 20 to be inserted into the slot 30 has a base part 21, a handle part 22, and the joint part 23 that couples the base part 21 and the handle part 22 to each other.

The base part 21, which is to be inserted into the slot 30, is shaped to conform to the shape of the slot 30. That is, the base part 21 is shaped so that the base part 21 can be fitted into the slot 30. In this embodiment, the slot 30 has a substantially cylindrical shape, and therefore, the base part 21 of the inner part 20 has a substantially cylindrical shape with a notch formed therein. The inner part 20 having such a shape has a higher section modulus and a higher strength than the thin-plate-like slide member of the example of the related art described earlier. Therefore, the inner part 20 is less susceptible to damage even if an external force is applied thereto.

The base part 21 has a socket 24 for holding the wire. The socket 24 is shaped considering the cross-section of the wire and desired forces to be applied to the wire during the orthodontic treatment of a patient. If during the treatment different forces are required to be applied to the wire than the current forces, then the inner part can be replaced with a new one having the socket designed to provide the proper forces; thereby avoiding the need to change the bracket bonded to the tooth of a patient. The shape of the socket 24 can be circular, square, rectangular, or any other desired shape depending upon the archwire used.

Figure 2A:
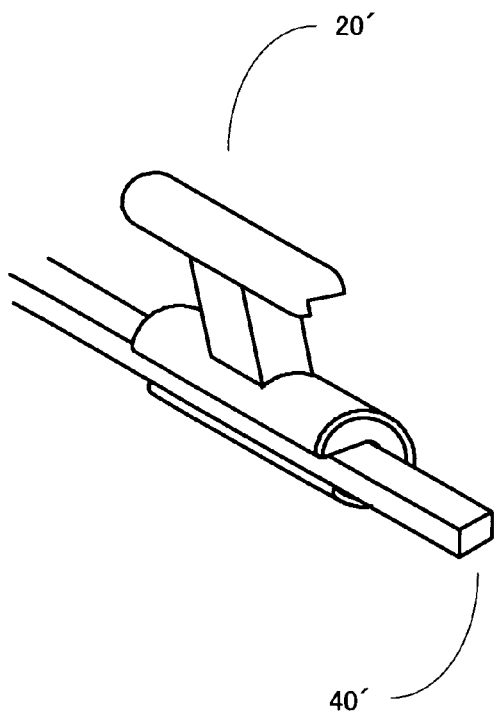
FIG. 2A shows a perspective view of the inner part with the socket shaped to hold a rectangular wire.
Figure 2B:
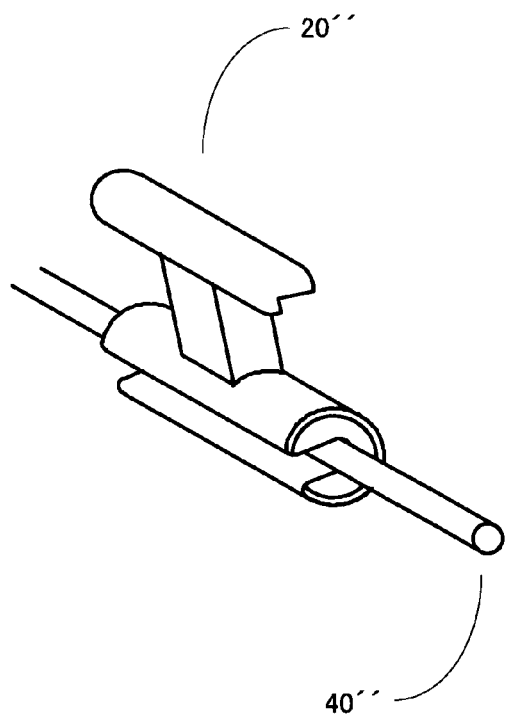
FIG. 2B shows a perspective view of the inner part with the socket shaped to hold a round wire.

The base part 21 as shown in FIG. 2 has the socket 24 for holding the wire 40 having a circular cross section. The socket 24 is formed by cutting a part of the base part 21 to form a space for housing the wire 40 in the base part 21. In this embodiment, the base part 21 having the socket 24 has a substantially C-shaped cross section and has an outward opening. Specifically, the socket 24 is defined by a bottom part 24a and side surfaces 24b and 24c, the bottom part 24a is an arc-shaped surface, and the side surfaces 24b and 24c are flat surfaces. The side surfaces 24b and 24c are inclined and diverge outwardly to form the opening. The wire 40 is inserted into the opening. Alternate example configurations for the slot for holding different shapes of wires are shown in FIGS. 2A and 2B. FIG. 2A shows a perspective view of the inner part 20' with the socket shaped to hold a rectangular wire 40'. In this case the bottom part and the side surfaces of the socket are all flat surfaces.

Similarly, FIG. 2B shows a perspective view of the inner part 20" with the socket shaped to hold a round wire 40". In this case the bottom part of the socket has a semi-circular surface and the side surfaces of the socket are flat surfaces.

The handle part 22 is coupled to the base part 21. Specifically, the joint part 23 is connected to the outer perimeter of the base part 21 at one end and to the handle part 22 at the other end. The handle part 22 has a recess 25 formed therein. The recess 25 opens toward the joint part 23 and is engaged with a protrusion 14 formed on the back surface of the lower arm portion 13 when the handle part 22 is rotated downwardly.

The bracket 10 and the inner part 20 are each configured as described above. The two components are assembled as described below.

The inner part 20 and the slot 30 are placed side by side so that the arc-shaped outer perimeter of the inner part 20 and the arc-shaped surfaces 12a and 13a of the slot 30 are aligned with each other, and the opening 32 of the slot 30 and the joint part 23 are aligned each other. Then, the inner part 20 is moved horizontally and inserted into the slot 30. When the joint part 23 enters the vertical slit 31, the horizontal movement of the inner part 20 is stopped, and the inner part 20 is rotated by vertically moving the handle part 22. Then, as shown in FIG. 3, the opening 32 and the opening of the socket 24 of the inner part 20 are substantially aligned with each other. In this state, when the wire 40 is inserted into the opening 32, the wire 40 reaches to the bottom part 24a of the socket 24 because the opening 32 and the opening of the socket 24 are aligned with each other.

Figure 4:
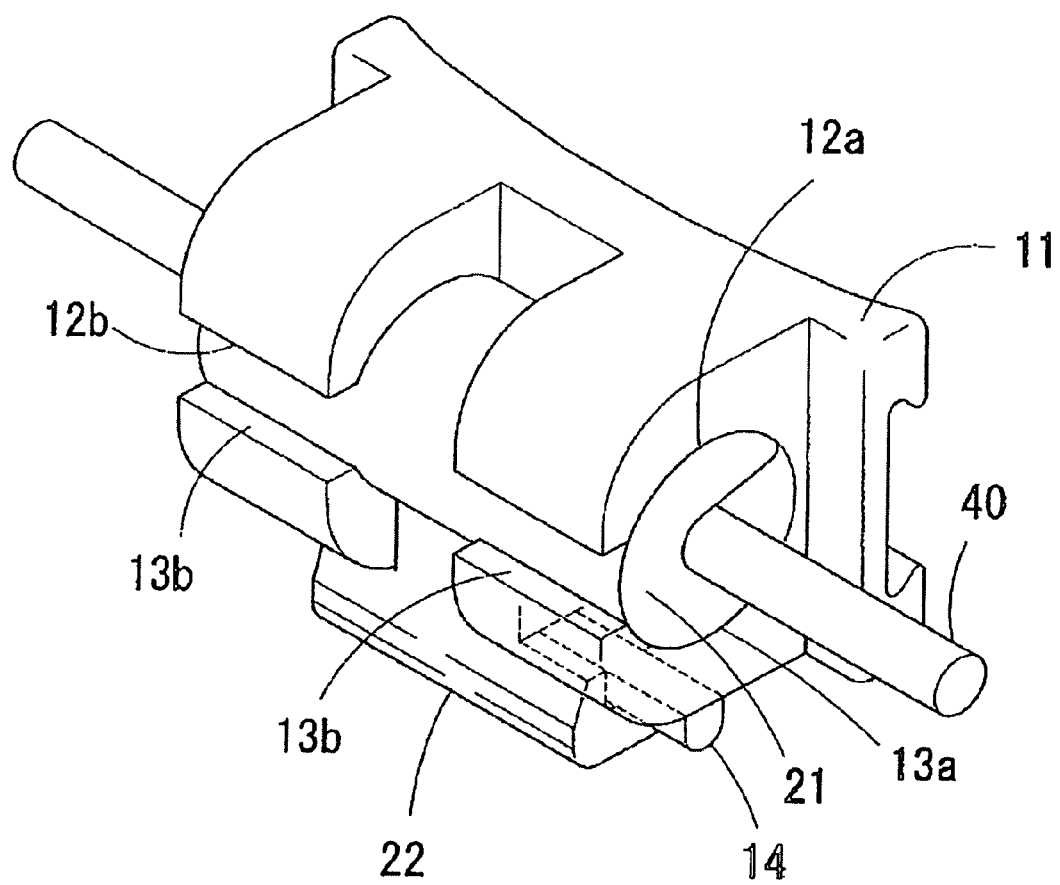
FIG. 4 is a perspective view of the inner part inserted in the bracket in the embodiment 1 of the present invention.

Once the wire 40 is inserted into the socket 24, the handle part 22 is moved downwardly to rotate the inner part 20 again. As the inner part 20 rotates, the opening of the socket 24 moves away from the opening 32 of the slot 30, and the two openings become displaced from each other. Thus, as shown in FIG. 4, the opening 32 is closed with a part of the inner part 20 other than the socket 24 (the part opposite to the socket 24). In this way, the wire 40 is held in the bracket 10.

Referring to FIG. 4 again, at this time, the recess 25 in the handle part 22 is engaged with the protrusion 14 on the lower arm portion 13 to help keep the wire 40 held in the inner part 20. Since the joint part 23 is positioned in the vertical slit 31, the inner part 20 is prevented from moving horizontally. In this way, the wire 40 is held with higher reliability. The same description also applies when the wire is square or rectangular or any other shape.

In the above description, the wire 40 is inserted after the inner part 20 is fitted into the bracket 10. Alternatively, of course, the wire 40 can be inserted before the inner part 20 is inserted into the bracket 10. The same description also applies when the wire is square or rectangular or any other shape.

FIGS. 2C1-2H3 show different shapes of the socket of the inner part for providing different forces during orthodontic treatments of patients. Each group of these figures, 2C1-2C3, 2D1-2D3, 2E1-2E3, 2F1-2F3, 2G1-2G3, and 2H1-2H3, shows three views of the inner part, namely, front view 20F, top view 20T, and cross-sectional view 20C. The cross-sectional view 20C is taken at the cross sectional plane formed by A-A' cutting the front view 20F.

FIG. 2C1 shows the top view 20T, FIG. 2C2 shows the front view 20F, and FIG. 2C3 shows the cross-sectional view 20C of the socket shaped to provide 22 degrees torque as shown in FIG. 2C3. As further shown in FIG. 2C3, the angle of opening of the socket 24' is selected depending on the desired torque. The angle of inclination of the axis line L' with respect to the axis line L determines the torque, which is 22 degrees in FIG. 2C3. Axis line L' passes through the center of the bottom surface 24a' and is perpendicular to the bottom surface 24a'. The axis line L passes through the center of the base part 21' and along the centerline of the joint part 23'. With such a configuration, different torque depending on the angle of opening of the socket 24' can be applied. When applying a torque to a tooth surface, if inner parts having differently angled sockets are prepared, a desired torque can be applied only by selecting the appropriate inner part without changing the bracket. Therefore, the wire can be attached in a relatively short time, and the treatment time can be reduced.

FIGS. 2D1, 2D2 and 2D3 show the top view 20T, the front view 20F and the cross-sectional view 20C, respectively, of the socket shaped to provide 7 degrees angulation as shown in FIG. 2D2. As further shown in FIG. 2D2, the angulation is determined by the inclination angle between the top surface 24'b of the slot 24' and the horizontal surface H, which is 7 degrees. The top surface 24'b and 24'c remain parallel.

FIGS. 2E1, 2E2 and 2E3 show the top view 20T, the front view 20F and the cross-sectional view 20C, respectively, of the socket shaped to provide 4 degrees rotation as shown in FIG. 2E1. As further shown in FIG. 2E1, in order to provide the rotation, the width of the bottom surface 24'a at one end is made greater than at the other end. The rotation is determined by the inclination angle between the top surface 24'b of the slot 24' and the horizontal surface H, which is 4 degrees. The top surfaces 24'b and 24'c do not remain parallel in this case.

FIGS. 2F1, 2F2 and 2F3 show the top view 20T, the front view 20F and the cross-sectional view 20C, respectively, of the socket shaped to provide translation. As further shown in FIG. 2F3, in order to provide translation, either the position of the socket 24' with respect to the slot 30 is adjusted by positioning it up or down, or the depth D of the socket 24' is increased or decreased. Increasing the depth D of the socket 24' will bring the bottom surface of the socket 24' closer to the inner surface of the slot 30, shown in FIG. 1; and decreasing the depth D of the socket 24' will move the bottom surface of the socket 24' away from the inner surface of the slot 30.

FIGS. 2G1, 2G2 and 2G3 show the top view 20T, the front view 20F and the cross-sectional view 20C, respectively, of the socket shaped to provide combination of 22 degrees torque (FIG. 2G3) and 4 degrees rotation (FIG. 2G1).

This is achieved by combining the process described above with respect to FIG. 2C3 with the process described above with respect to FIG. 2E1.

FIGS. 2H1, 2H2 and 2H3 show the top view 20T, the front view 20F and the cross-sectional view 20C, respectively, of the socket shaped to provide combination of 7 degrees angulation and 4 degrees of rotation. This is achieved by combining the process described above with respect to FIG. 2D2 with the, process describe above with respect to FIG. 2E1.

Although other combinations of forces are not described above, one skilled in the art would be able to do so.

The bracket 10 is made of a dental metal, a synthetic material, a ceramic or a synthetic resin, for example, or any other suitable material. Similarly, the inner part 20 is made of a dental metal, a synthetic material, a ceramic or a synthetic resin, for example, or any other suitable material. The bracket 10 and the inner part 20 both may be made of the same material or of different materials. Examples of the synthetic resin include polymethyl methacrylate, polyoxymethylene, polycarbonate, polypropylene, polyethylene and polyethylene naphthalate. Many conventional orthodontic devices use metals for strength reasons. However, the orthodontic device according to the present invention has a simple structure and therefore can be reduced in size while maintaining a sufficient strength, so that the orthodontic device need not be made of a metal and can be made of a plastic or ceramic. Furthermore, since the orthodontic device has a simple structure and therefore can be reduced in size as described above, the orthodontic device is inconspicuous when attached to the teeth surface and is aesthetically pleasing. Thus, the orthodontic device puts reduced psychological and physical burdens on patients and therefore is preferable.

The bracket 10 has a width of about 2.8 to 3.5 mm, a height of about 2.5 mm and a depth of about 2.0 mm. The base portion 11 has a thickness of 0.45 mm, and the upper (lower) arm portion has a thickness (in the vertical direction) of about 0.1 mm at the base end thereof and a thickness (in the vertical direction) of about 0.25 mm at the tip end thereof. The vertical slit has a horizontal width of about 0.8 mm, and the opening 32 of the slot 30 has a vertical width of 0.7 mm. The cylindrical slot 30 has a diameter of about 1.3 mm and has a horizontal length of about 2.5 to 3.2 mm. The substantially cylindrical base part 21 of the inner part 20 has a diameter of about 1.3 mm, and the joint part has a thickness (d) of about 0.7 mm and a horizontal width (W) of about 0.8 mm. The depth of the groove of the socket is about 0.9 mm. The wire 40 has a diameter of about 0.012 to 0.020 inch.

The bracket 10 and the inner part 20 may be customized for a patient or may be selected from commercially available such products.

In summary, with the invention disclosed herein, once a bracket is bonded to a tooth of a patient, it does not have to be removed during the entire orthodontic treatment of the patient. Desired forces, such as torque, angulation, rotation or translation, or any combination of such forces can be achieved through the inner part. Inner part can be replaced with another one at any time during the orthodontic treatment. Bracket replacement can be eliminated. This would help the orthodontic treatment of a patient a great deal—it will be more comfortable, quicker and less expensive.

In case the wire design prevents rotation of the inner part, thereby preventing closure of the bracket slot opening, then the inner part can still be used only for treatment purposes where the inner part is replaced as dictated by the treatment without having to replace the bracket bonded to the tooth. As for holding the wire in its position under such conditions, some other mechanics can be used along with the inner part for the treatment.

Embodiment 2

FIGS. 1 and 5 to 10 show an embodiment 2 of the present invention.

An orthodontic device according to the embodiment 2 includes a bracket 10 and an inner part 50. The bracket 10 in the embodiment 2 has the same structure as in the embodiment 1, but the inner part 50 has different structure.

Figure 5:
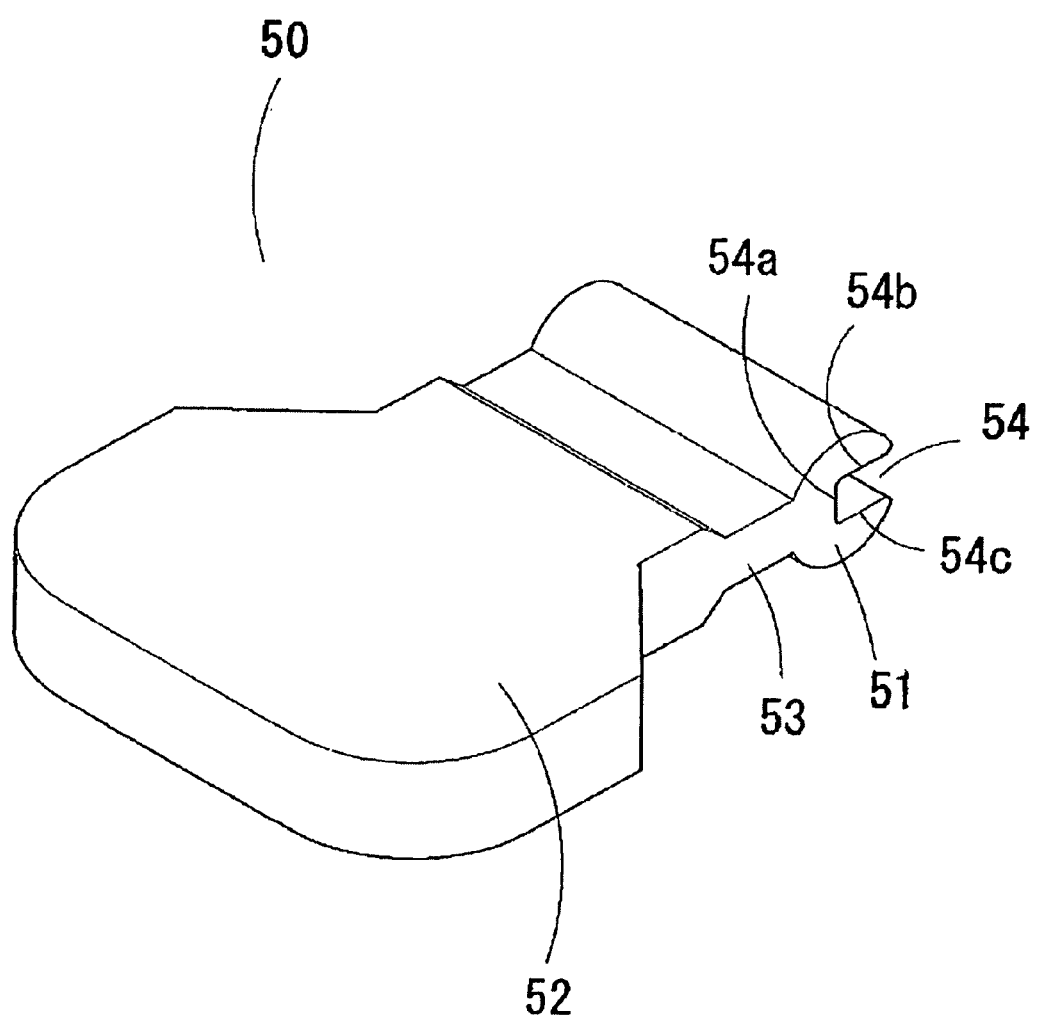
FIG. 5 is a perspective view of an inner part according to the embodiment 2 of the present invention.

As shown in FIG. 5, the inner part 50 has a base part 51, a handle part 52 and a joint part 53. The base part 51 is to be inserted into a slot 30 and therefore shaped to conform to the shape of the slot 30. In this embodiment, the slot 30 has a substantially cylindrical shape, and therefore, the base part 51 also has a substantially cylindrical shape with a notch formed therein. The notch formed in the base part 51 constitutes a socket 54 for holding a wire 60 having a rectangular cross section. The socket 54 is shaped to conform to the rectangular shape of the wire 60. Specifically, referring to FIG. 8 and the like, the socket 54 is defined by opposite side surfaces 54b and 54c and a bottom surface 54a perpendicular to the side surfaces 54b and 54c. In the embodiment 2, the cross section of the wire can be any polygon and is not limited to the shape described in this embodiment and shown in the drawings.

Figure 8:
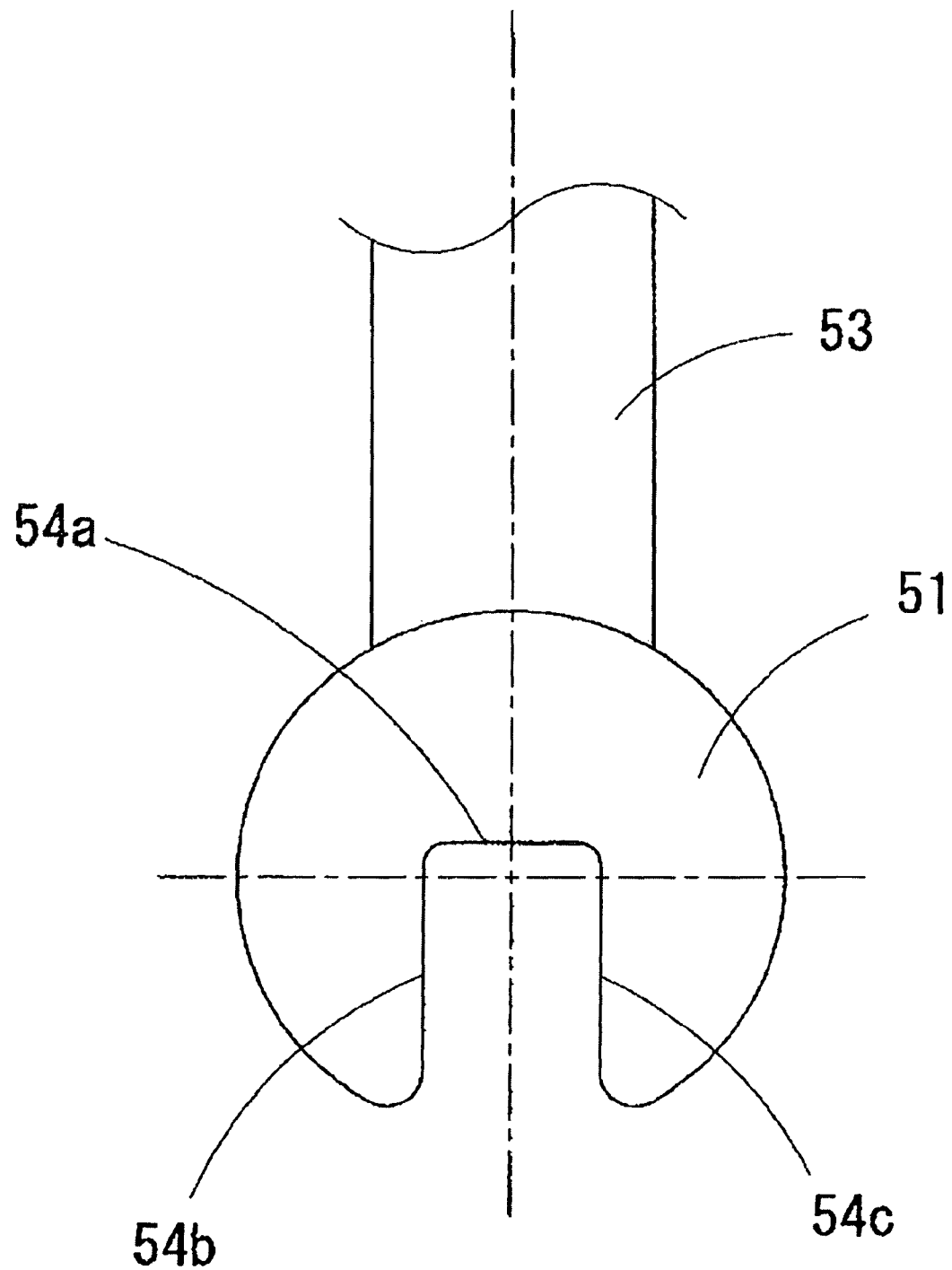
FIG. 8 is a perspective view of the inner part (the angle of opening equals to 0 degrees) according to the embodiment 2 of the present invention.
Figure 9:
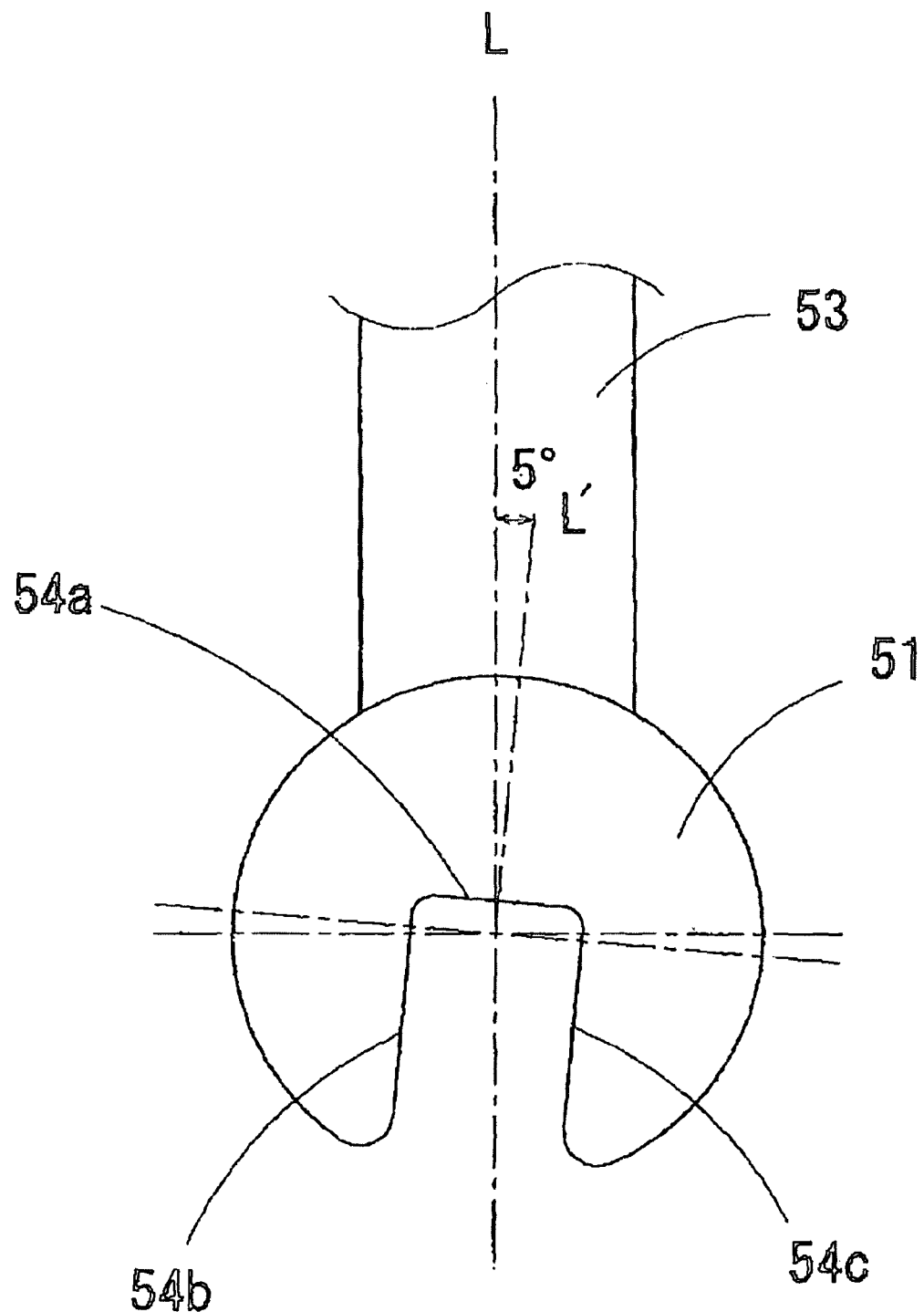
FIG. 9 is a perspective view of the inner part (the angle of opening equals to 5 degrees) according to the embodiment 2 of the present invention.
Figure 10:
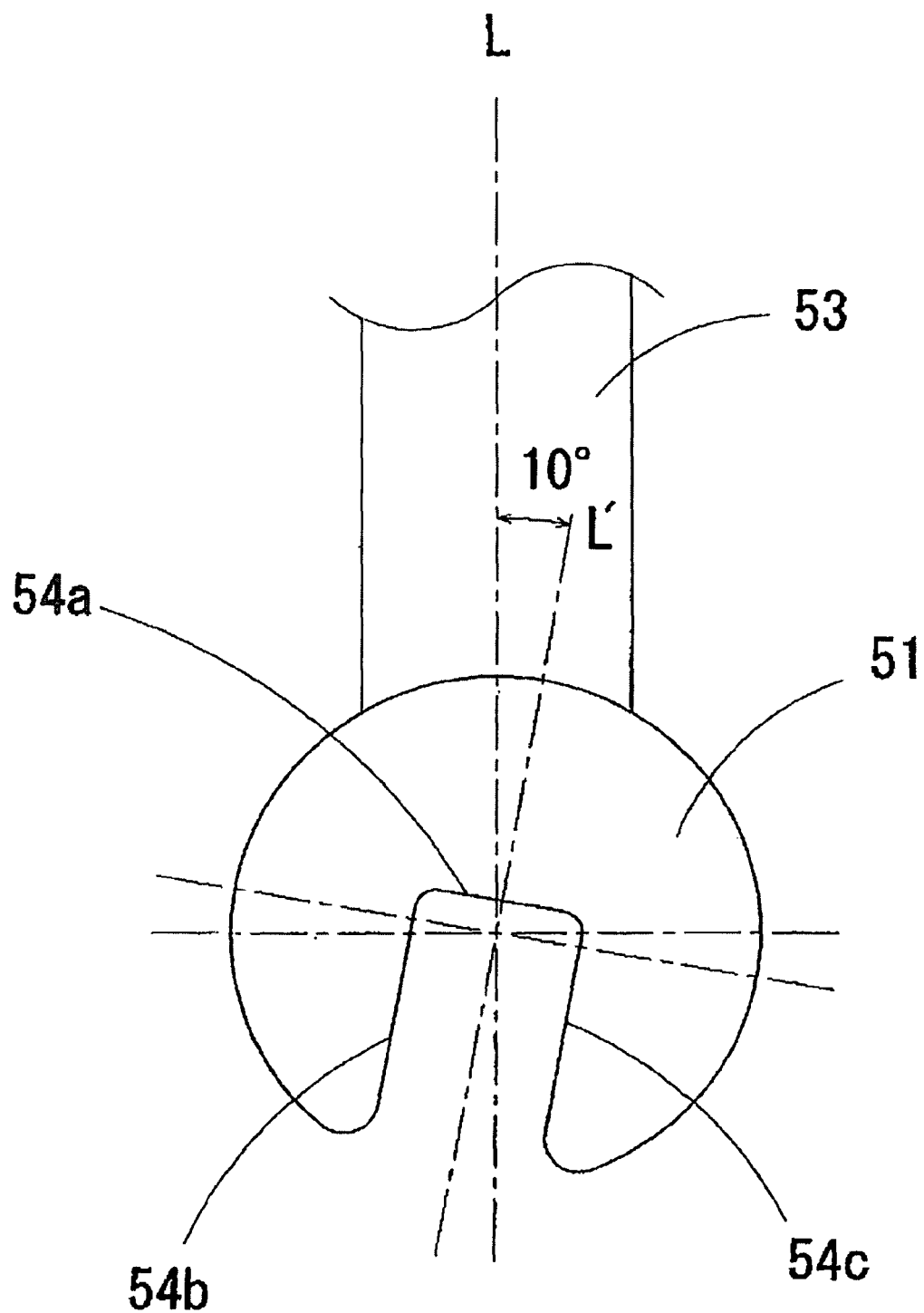
FIG. 10 is a perspective view of the inner part (the angle of opening equals to 10 degrees) according to the embodiment 2 of the present invention.
Figure 11:
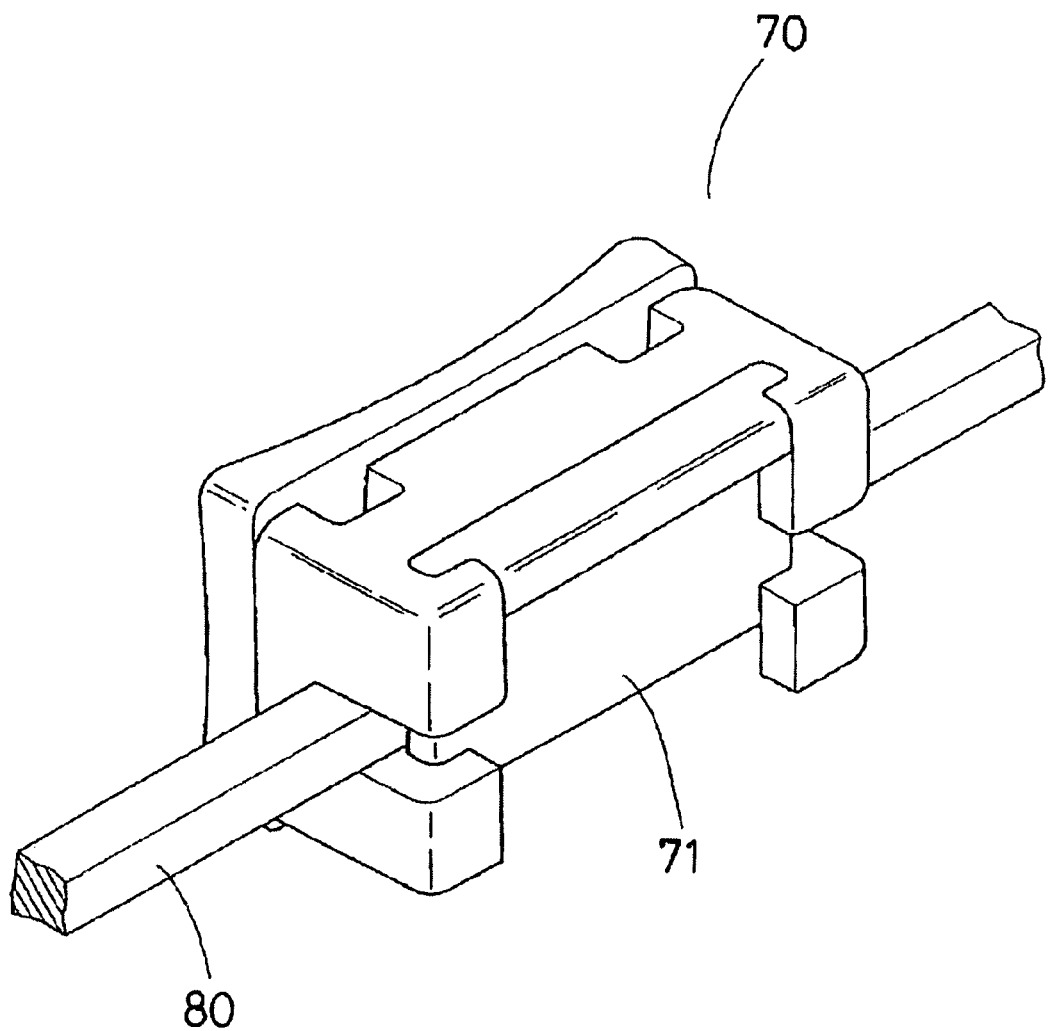
FIG. 11 is a perspective view of an example of the related art.
Figure 12:
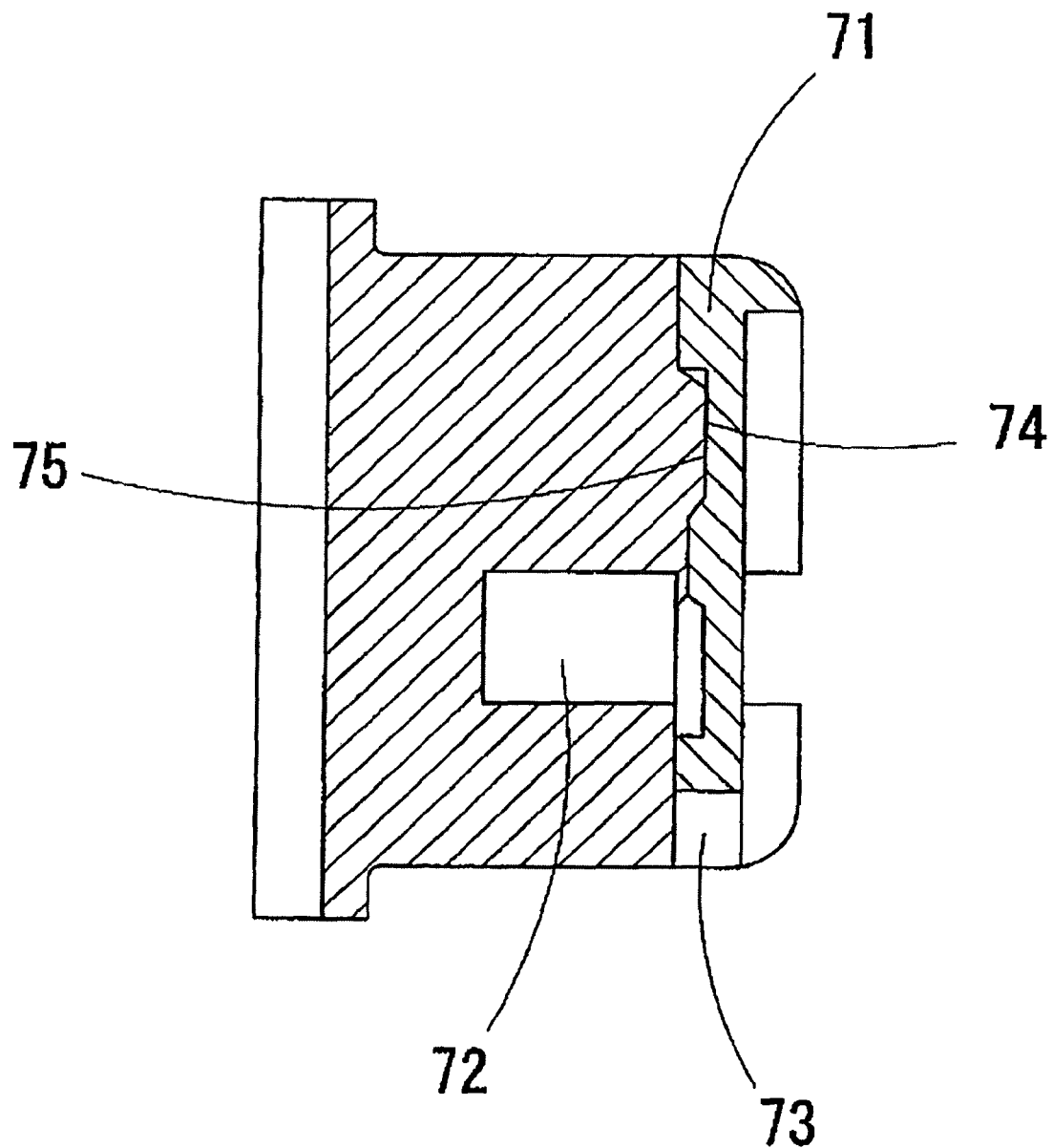
FIG. 12 is a cross-sectional view of the example of the related art shown in FIG. 11.

Here again, the direction (angle) of opening of the socket 54 is appropriately selected. The angle of opening of the socket 54 is selected depending on a desired torque or rotation. For example, as shown in FIGS. 8 to 10, the angle of inclination of an axis line L', which passes through the center of the bottom surface 54a perpendicular to the bottom surface 54a, with respect to an axis line L, which passes through the center of the base part 51 (center of the circle) and along the centerline of the joint part 53, is selected to be 0 degrees, 5 degrees or 10 degrees, for example. With such a configuration, different torque depending on the angle of opening of the socket 54 can be applied. When applying a torque to a tooth surface, if inner parts having differently angled sockets are prepared, a desired torque can be applied only by selecting the appropriate inner part without changing the bracket. Therefore, the wire can be attached in a relatively short time, and the treatment time can be reduced.

The handle part 52 is to facilitate handling of the inner part 50 and is coupled to the base part 51 by the joint part 53. The handle part 52 is used when inserting the inner part 50 into the slot 30. The handle part 52 has a width of about 8.0 mm and a length of about 7.0 mm. As described later, the handle part 52 is cut away and separated from the base part 51.

Now, assembly of the bracket 10 and the inner part 50 will be described.

Figure 6:
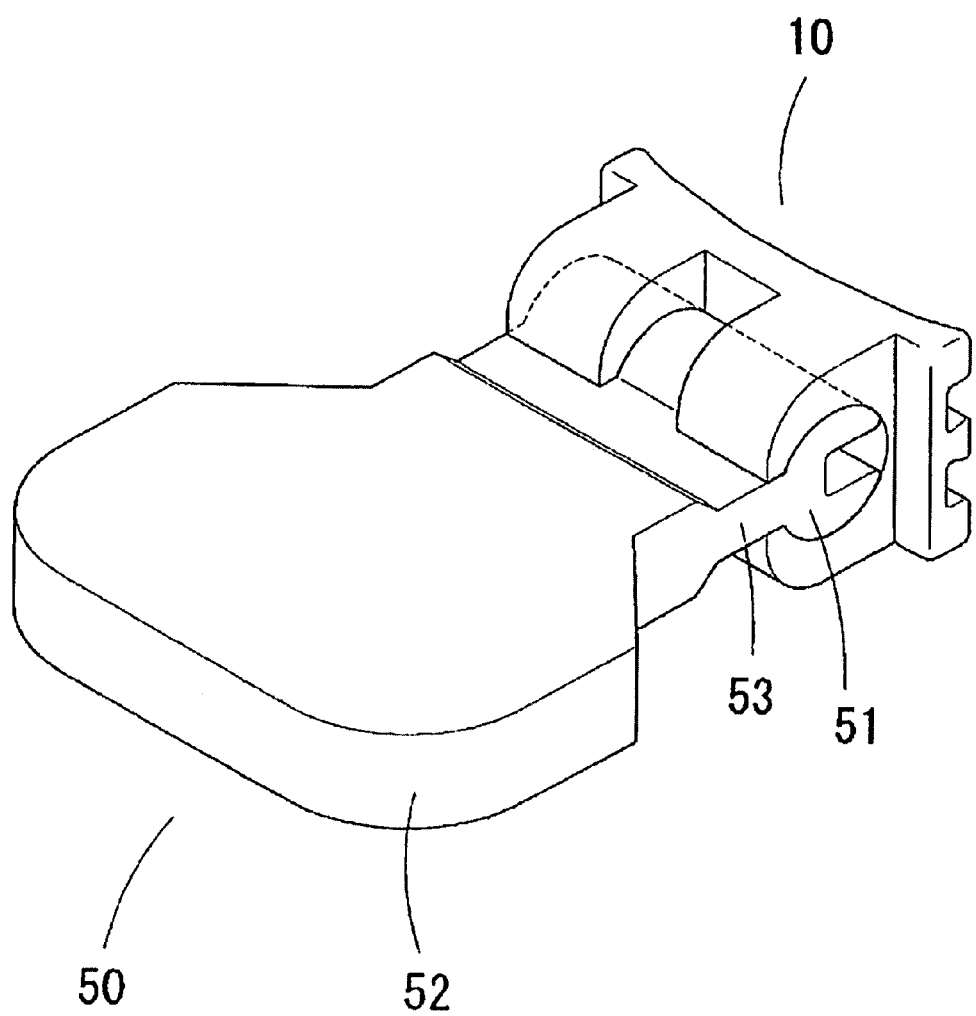
FIG. 6 is a perspective view of the inner part inserted in the bracket in the embodiment 2 of the present invention.
Figure 7:
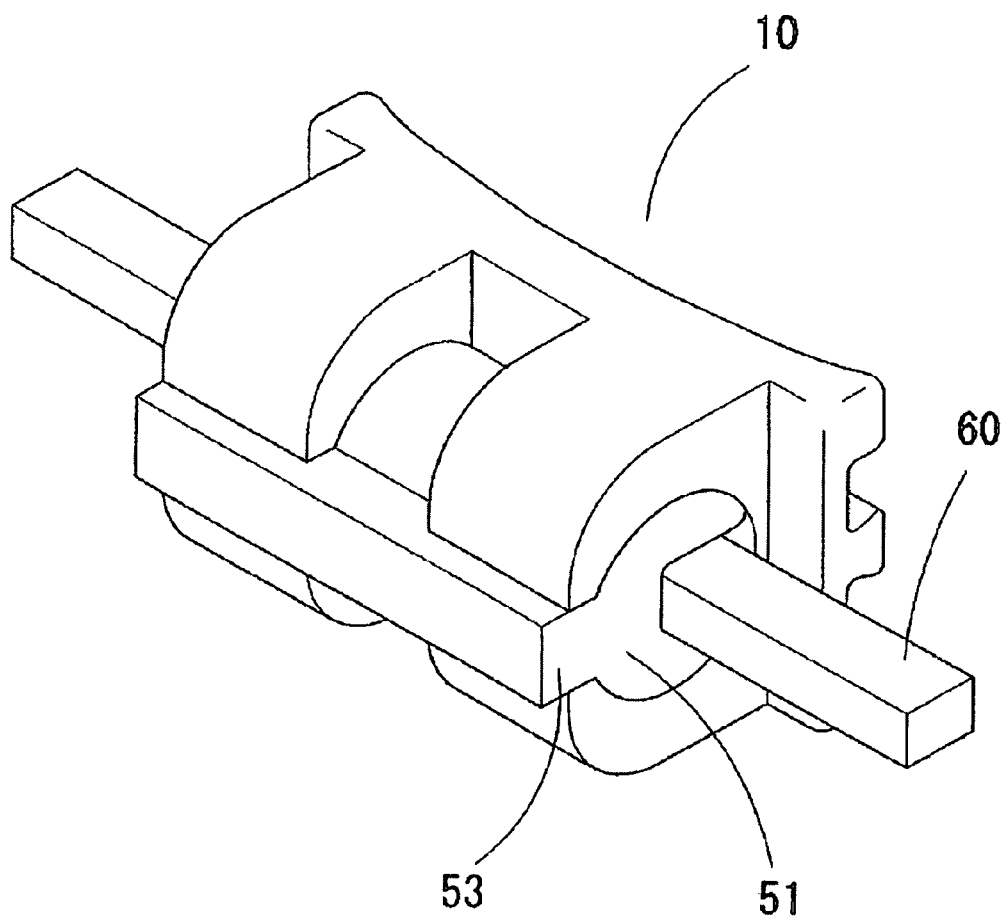
FIG. 7 is a perspective view of the inner part shown in FIG. 6 from which a base part thereof has been cut away in the embodiment 2 of the present invention.

The wire 60 having a rectangular cross section is inserted into the slot 30, and then, the inner part 50 is inserted into the slot 30. Specifically, after the wire 60 is inserted into the slot 30 through an opening 32, the inner part 50 and the slot 30 are placed side by side so that the arc-shaped outer perimeter of the inner part 50 and the arc-shaped inner surfaces (arc-shaped surfaces 12a and 13a) of the slot 30 are aligned with each other, and the opening 32 and the joint part 53 are aligned each other. Then, the inner part 50 is moved horizontally and inserted into the slot 30. When the entire inner part 50 is housed in the slot 30 as shown in FIG. 6, the handle part 52 is cut away. The inner part 50 from which the handle part 52 is removed is composed of the base part 51 and the joint part 53, and as shown in FIG. 7, the joint part 53 is positioned in the opening 32 of the slot 30 to close the opening 32. At this time, the inner part 50 (joint part 53) is held between a surface 12b of the upper arm portion 12 and a surface 13b of the lower arm portion 13 and therefore is prevented from rotating (moving) vertically, and a torque is applied to the teeth in this state.

The handle part 52 has a width of about 8.0 mm and a length of about 7.0 mm. The dimensions of the wire 60 are appropriately selected. For example, a rectangular wire having a height of 0.016 mm and a width of 0.022 mm, a height of 0.018 mm and a width of 0.025 mm, a height of 0.021 mm and a width of 0.025 mm, or a height of 0.017 mm and a width of 0.027 mm is used.

In summary then, the invention described above discloses an orthodontic device consisting of two parts: (a) a bracket, and (b) an inner part. The bracket is bonded to a tooth of a patient. The inner part is movable and removable and is placed in the slot of the bracket. The socket in the inner part is shaped to hold an orthodontic wire and apply desired forces to the wire for orthodontic treatment of a patient. When forces applied to the wire need to be changed during the treatment of a patient the inner part can be replaced with a different suitable inner part without replacing the bonded bracket. This is a major advantage of the orthodontic device disclosed herein over the standard bracket which requires debonding of the current bracket and bonding of the new bracket. Furthermore, the inner part disclosed herein can be positioned to hold the wire in place.

We claim:

1. An orthodontic device, comprising:
   a bracket and an inner part;
   wherein said bracket comprises a base portion having a back surface designed for bonding said bracket to a tooth surface during orthodontic treatment of a patient, an upper arm portion extending forward from a front surface of said base portion, and a lower arm portion extending forward from said front surface of said base portion; wherein an arc-shaped surface of said upper arm portion and an arc-shaped surface of said lower arm portion facing each other form a slot on said front surface;
   wherein said inner part has a base part, a handle part, and a joint part connecting an outer perimeter of said base part on one end and said handle part on an opposing end;
   wherein said handle part has a recess, said recess being formed to engage a protrusion part disposed on a back surface of said lower arm portion;
   wherein said inner part is designed to be inserted into said slot and has a socket; said socket shaped to hold a wire and exert desired forces to said wire during orthodontic treatment of said patient;
   wherein said upper arm portion has a shape of a hook, and tip part of said upper arm portion is curved to cover an outer perimeter of said inner part;
   wherein said lower arm portion has a shape of a hook, and tip part of said lower arm portion is curved to cover said outer perimeter of said inner part;
   wherein said inner part is inserted in said slot, and said inner part is held stably between said arc-shaped surface of said upper arm portion and said arc-shaped surface of said lower arm portion;
   wherein said inner part can be removed and replaced with another inner part to realize different forces applied to said wire without having to remove said bracket bonded to said tooth.

2. The orthodontic device according to claim 1, wherein a horizontal width of said slot and a horizontal width of said inner part are substantially equal to each other.

3. The orthodontic device according to claim 1, wherein said base part has a part cutoff therein, thereby creating said socket with an opening in said base part.

4. The orthodontic device according to claim 1, wherein said joint part in combination with said base part closes said socket once said base part is entirely inserted into said slot, thereby reliably holding a wire inserted in said socket.

5. The orthodontic device according to claim 1, wherein said socket is shaped to conform to hold a rectangular shape wire.

6. The orthodontic device according to claim 1, wherein said socket is shaped to conform to hold a square shape wire.

7. The orthodontic device according to claim 1, wherein said socket is shaped to conform to hold a polygonal shape wire.

8. The orthodontic device according to claim 1, wherein said upper arm portion and said lower arm portion have a vertical slit with respect to said slot.

9. The orthodontic device according to claim 1, wherein said bracket and said inner part are made of a dental metal, a synthetic material, a ceramic, or a synthetic resin.

10. The orthodontic device according to claim 1, wherein said inner part is shaped to provide desired torque.

11. The orthodontic device according to claim 1, wherein said inner part is shaped to provide desired angulation.

12. The orthodontic device according to claim 1, wherein said inner part is shaped to provide desired rotation.

13. The orthodontic device according to claim 1, wherein said inner part is shaped to provide desired translation.

14. The orthodontic device according to claim 1, wherein said inner part is shaped to provide desired combination of two or more forces such as torque, angulation, rotation and translation.

15. An orthodontic device, comprising:
    a bracket and an inner part;
    wherein said bracket comprises a base portion having a back surface designed for bonding said bracket to a tooth surface during orthodontic treatment of a patient, an upper arm portion extending forward from a front surface of said base portion, and a lower arm portion extending forward from said front surface of said base portion; wherein an arc-shaped surface of said upper arm portion and an arc-shaped surface of said lower arm portion facing each other form a slot on said front surface;
    wherein said inner part has a base part, a handle part, and a joint part connecting an outer perimeter of said base part on one end and said handle part on an opposing end;
    wherein said handle part facilitates easy insertion of said inner part into said slot;
    wherein said inner part has a socket;
    wherein said slot and said socket together reliably hold a wire into said bracket during said treatment;
    wherein said socket has three surfaces specifically shaped to accommodate said wire;
    wherein said socket is further shaped to apply desired forces to said wire during said treatment;
    wherein said upper arm portion has a shape of a hook, and tip part of said upper arm portion is curved to cover an outer perimeter of said inner part;
    wherein said lower arm portion has a shape of a hook, and tip part of said lower arm portion is curved to cover said outer perimeter of said inner part;
    wherein said inner part is inserted in said slot and said inner part is held stably between arc-shaped surface of said upper arm portion and said arc-shaped surface of said lower arm portion; and
    wherein said inner part can be removed and replaced with another inner part to realize different forces without having to remove said bracket bonded to said tooth.

16. The orthodontic device according to claim 15, wherein said handle part can be removed after said inner part is inserted into said slot.

17. The orthodontic device of claim 15, wherein said desired forces applied to said wire comprise torque.

18. The orthodontic device of claim 15, wherein said bracket and said inner part are made of either a dental metal, or a synthetic material, or a ceramic or a synthetic resin.

19. The orthodontic device of claim 18, wherein said synthetic resin is either polymethyl methacrylate, or polyoxymethylene, or polycarbonate, or polypropylene, or polyethylene or polyethylene naphthalate.

20. The orthodontic device according to claim 15, wherein said socket is shaped to hold a rectangular wire; and wherein said socket is angled relative to an axis line perpendicular to bottom surface of said socket.

21. The orthodontic device of claim 15, wherein said socket is shaped to hold a wire having a circular cross section.

22. The orthodontic device of claim 15, wherein said socket is shaped to hold a wire having a rectangular cross section.

23. The orthodontic device of claim 15, wherein said socket is shaped to hold a wire having a polygonal cross section.

\* \* \* \* \*